United States Patent
Ding et al.

(10) Patent No.: US 8,795,648 B2
(45) Date of Patent: *Aug. 5, 2014

(54) POLY(BETA MALIC ACID) WITH PENDANT LEU-LEU-LEU TRIPEPTIDE FOR EFFECTIVE CYTOPLASMIC DRUG DELIVERY

(71) Applicant: Cedars-Sinai Medical Center, Los Angeles, CA (US)

(72) Inventors: Hui Ding, Los Angeles, CA (US); Julia Y. Ljubimova, Studio City, CA (US); Eggehard Holler, Los Angeles, CA (US); Keith L. Black, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 11 days.

This patent is subject to a terminal disclaimer.

(21) Appl. No.: 13/646,947

(22) Filed: Oct. 8, 2012

(65) Prior Publication Data

US 2013/0084261 A1    Apr. 4, 2013

Related U.S. Application Data

(63) Continuation of application No. 12/935,110, filed as application No. PCT/US2009/040252 on Apr. 10, 2009, now Pat. No. 8,309,614.

(60) Provisional application No. 61/044,191, filed on Apr. 11, 2008.

(51) Int. Cl.
*A61K 47/14* (2006.01)
*C12N 15/11* (2006.01)
*C07H 21/04* (2006.01)

(52) U.S. Cl.
USPC ...... 424/78.17; 514/44 A; 514/772; 536/24.5; 977/704; 977/906

(58) Field of Classification Search
None
See application file for complete search history.

(56) References Cited

U.S. PATENT DOCUMENTS

| 7,056,704 B2 | 6/2006 | Tuschl et al. |
| 7,935,677 B2 | 5/2011 | Ljubimova et al. |
| 8,309,614 B2 * | 11/2012 | Ding et al. ............ 514/772 |
| 2007/0259008 A1 * | 11/2007 | Ljubimova et al. ........ 424/400 |

FOREIGN PATENT DOCUMENTS

CN   1615855 A   *   5/2005

OTHER PUBLICATIONS

Machine translation of CN 1615855 A, 2005.*
West record of CN 1615855 A, 2005.*
Coonrod, A., et al., "On the mechanism of DNA transfection: efficient gene transfer without viruses," Gene Therapy, 1997, 4:1313-1321.
Fujita, et al., "Brain tumor tandem targeting using a combination of monoclonal antibodies attached to biopoly(beta-L-malic acid)," Jour Controlled Release, Oct. 8, 2007, 122(3):356-363.
GenBank AAB52902.1 (1997).
Lee, Bong-Seop, et al., "Delivery of antisense oligonucleotides and transferrin receptor antibody in vitro and in vivo using a new multifunctional drug delivery system based on polymalic acid," Proc. Amer. Assoc. Cancer Res., 2004, vol. 45, Abstract #647.
Lee, Bong-Seop, et al., "Polycefin, a New Prototype of a Multifunctional Nanoconjugate Based on Poly(β-L-malic acid) for Drug Delivery," Bioconjugate Chem., 2006, 17:317-326.
Lutsenko, Svetlana, et al., "Biochemical Basis of Regulation of Human Copper-Transporting ATPases," Arch Biochem Biophys., Jul. 15, 2007, 463(2):134-148.
MDNSI, Molecular Oncology, Jul. 1, 2009, Available on the internet at URL:http://www.cedars-sinai.edu/10141.html.
PCT International Preliminary Report on Patentability (Chapter I of the Patent Cooperation Treaty) dated Oct. 21, 2010, for International Patent Application No. PCT/US2009/040252, filed Apr. 10, 2009.

* cited by examiner

*Primary Examiner* — Richard Schnizer
(74) *Attorney, Agent, or Firm* — Volpe and Koenig, P.C.

(57) ABSTRACT

The invention relates to the use of Polycefin-LLL nanoconjugate as a means of cytoplasmic delivery of drugs. In one embodiment, the present invention provides a drug delivery molecule, comprising a polymerized carboxylic acid molecular scaffold covalently linked to L-leucylleucylleucine. In another embodiment, the Polycefin-LLL includes drug antisense morpholino oligos, targeting antibodies, and a pH-sensitive endosome escape unit. In addition, the drug could be siRNA, microRNA, and aptamer.

17 Claims, 12 Drawing Sheets

(a)

(b)

(a)

(b)

SEQUENCE LISTING

<160> NUMBER OF SEQ ID NOS: 2

<210> SEQ ID NO 1
<211> LENGTH: 25
<212> TYPE: DNA
<213> ORGANISM: Homo sapiens

<400> SEQUENCE: 1

```
agctcaaagc catttctccg ctgac                                          25

<210> SEQ ID NO 2
<211> LENGTH: 25
<212> TYPE: DNA
<213> ORGANISM: Homo sapiens

<400> SEQUENCE: 2
ctagcaactg gagaagcccc atgcc                                          25
```

POLY(BETA MALIC ACID) WITH PENDANT LEU-LEU-LEU TRIPEPTIDE FOR EFFECTIVE CYTOPLASMIC DRUG DELIVERY

CROSS-REFERENCE TO RELATED APPLICATIONS

This application is a continuation of the U.S. patent application Ser. No. 12/935,110, filed Sep. 28, 2010 as the National Phase of International Application No. PCT/US2009/040252, filed Apr. 10, 2009, which claims the benefit of U.S. Provisional Patent Application No. 61/044,191, filed Apr. 11, 2008, which are incorporated by reference as if fully set forth.

GOVERNMENT RIGHTS

This invention was made with U.S. Government support under Grant Nos R01CA123495, R01CA136841 and U01CA151815 awarded by the National Cancer Institute. The Government may have certain rights in the invention.

The sequence listing titled "Sequence_Listing" which was created on Sep. 5, 2012, had a file size of 659 bytes, and filed with this application is incorporated by reference herein as if fully set forth.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Treatments using nucleic acid-based drugs such as DNA, antisense oligonucleonucleotides, small interfering RNA (siRNA), micro-RNA and/or aptamers are attractive but sometimes challenging. For example, nucleic acid-based drugs that specifically target oncogenes have the potential to block the unique initiation and propagation pathways of cancer cells, but their clinical application can be hindered due to the lack of safe and efficient drug delivery systems. Besides being non-toxic and non-immunogenic, an ideal drug delivery system for nucleic acid-based therapeutics must be able to assist the escape of therapeutics from the endosome so that the nucleic acid-based drug can be released into the cytoplasm where it can function.

Previously, it was believed that direct cytoplasmic delivery may be achievable using cell penetrating peptides (CPPs) which translocate across the cell membrane, thus bypassing the barrier of endosome and directly delivering their cargo into the cytoplasm (Elliott, G.; Cell 1997, 88, (2), 223-33). However, additional studies revealed that the internalization of most CPPs actually involve endocytosis (Trehin, R.; Eur J Pharm Biopharm 2004, 58, (2), 209-23). Moreover, most biomolecules are internalized by cells through endocytosis and are subsequently channeled into endosomal-lysosomal compartments, resulting in total loss of activity in lysosome if they do not possess the machinery to escape from the endosome. Thus, the endosome is a major barrier for cytoplasmic delivery of nucleic acid-based therapeutics and drug delivery systems must be designed to destabilize the endosome membrane to assist the escape of the therapeutics.

Thus, there is a need in the art for an effective cytoplasmic drug delivery system that can destabilize the endosome membrane.

SUMMARY OF THE INVENTION

Various embodiments include a drug delivery system, comprising a polymerized carboxylic acid molecular scaffold covalently linked to one or more biologically active molecular modules, where one of the one or more biologically active molecular modules comprises an endosome escape unit. In another embodiment, the polymerized carboxylic acid molecular scaffold is covalently linked to one or more biologically active molecular modules by a cleavable disulfide bond. In another embodiment, the endosome escape unit comprises L-leucylleucylleucine (LLL). In another embodiment, the endosome escape unit is pH sensitive. In another embodiment, one of the one or more biologically active molecular modules comprises an antisense Morpholino oligonucleotide. In another embodiment, one of the one or more biologically active molecular modules comprises an siRNA, a microRNA, and/or an aptamer. In another embodiment, one of the one or more biologically active molecular modules comprises at least one targeting module for promoting cellular uptake.

Other embodiments include a method of delivering a nucleic acid-based therapeutic to the cytoplasm of a cell, comprising providing a composition comprising a nucleic acid-based therapeutic covalently linked by cleavable disulfide bonds to a drug delivery system designed to destabilize an endosome membrane, and administering an amount of the composition effective to achieve a certain quantity of the nucleic acid-based therapeutic to the cell. In another embodiment, the cell is a glioma cell. In another embodiment, the drug delivery system comprises poly(.beta.-L-malic acid) (PMLA) containing about 40% of a pendant carboxylate conjugated by an amide bond. In another embodiment, the pendent carboxylate comprises trileucine.

Other embodiments include a method of synthesizing a drug delivery molecule, comprising providing a quantity of a Leu-Leu-Leu tripeptide, providing a quantity of a polymalic acid, and conjugating the Leu-Leu-Leu tripeptide with the polymalic acid. In another embodiment, the polymalic acid comprises PMLA. In another embodiment, the Leu-Leu-Leu tripeptide is conjugated with the polymalic acid by an amide bond.

Various embodiments also include methods of decreasing the volume of a glioma in an individual, comprising providing a composition that inhibits protein synthesis of Laminin-411, where the composition comprises PMLA covalently linked to a targeting antibody, a Laminin α4 antisense polynucleotide and/or β1 antisense polynucleotide, and a Leu-Leu-Leu tripeptide, and administering the composition to the individual at a concentration of up to but not exceeding 1 mg/mL. In another embodiment, the Laminin α4 antisense polynucleotide comprises a 5' to 3' polynucleotide sequence characterized by SEQ. ID. NO.: 1. In another embodiment, the Laminin β1 antisense polynucleotide comprises a 5' to 3' polynucleotide sequence characterized by SEQ. ID. NO.: 2. In another embodiment, the composition is administered systemically. In another embodiment, the composition is administered near the glioma. In another embodiment, the composition is administered by an intra-tumor injection. In another embodiment, the composition is administered by an implantable device. In another embodiment, the composition is administered subcutaneously, intraperitoneal and/or intravenously.

Other features and advantages of the invention will become apparent from the following detailed description, taken in conjunction with the accompanying drawings, which illustrate, by way of example, various embodiments of the invention.

DESCRIPTION OF THE INVENTION

Figure 1:
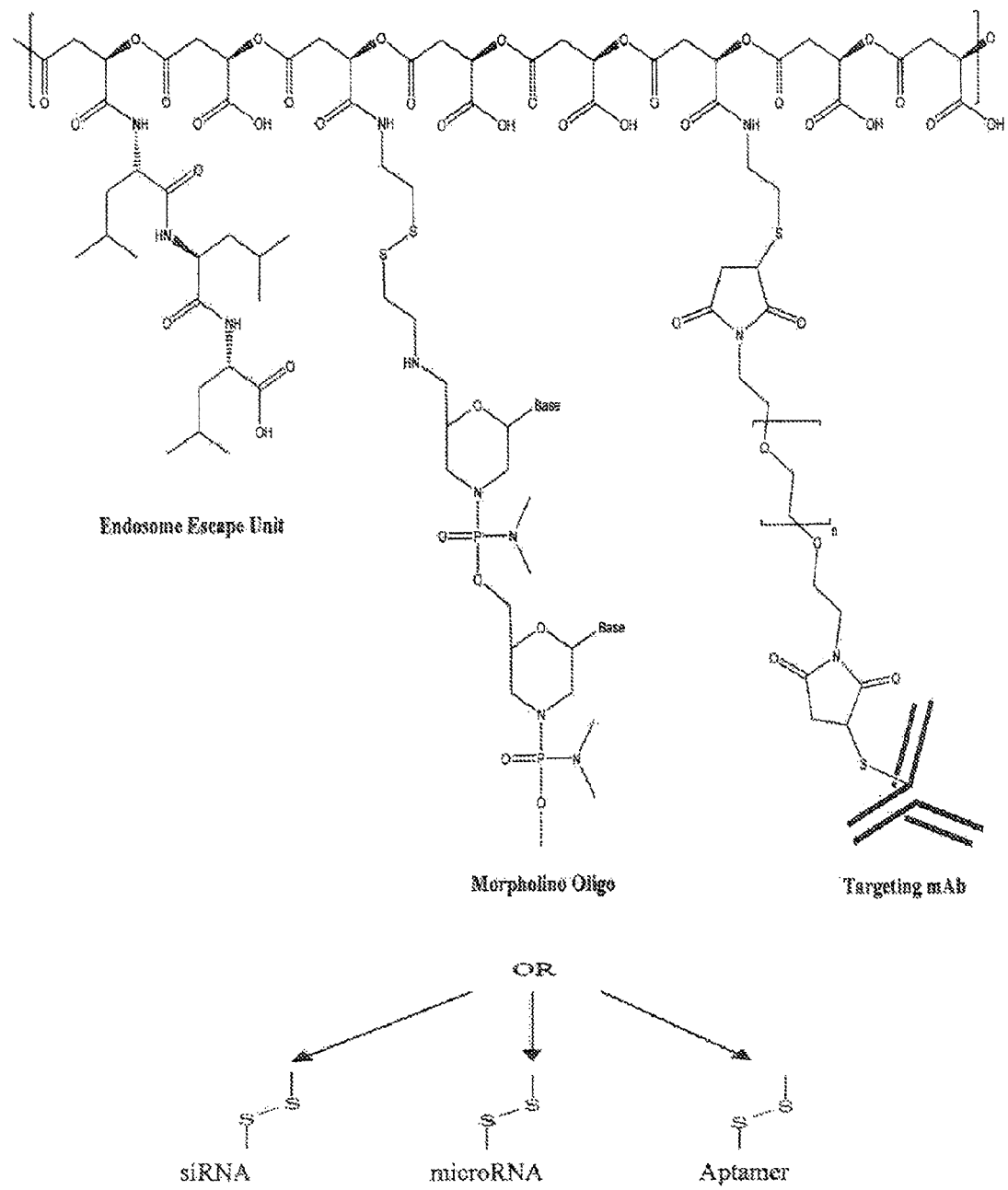
FIG. 1 depicts an example of a polymalic acid based drug carrier. The figure depicts a schematic structure of a minimal Polycefin variant. It contains three components, the drug Morpholino oligonucleotide, the endosome escape unit, and a targeting monoclonal antibody. In addition, other drugs, such as siRNA, microRNA and aptamer, can be attached to polycefin via disulfide bond for cytoplasmic delivery.
Figure 2:
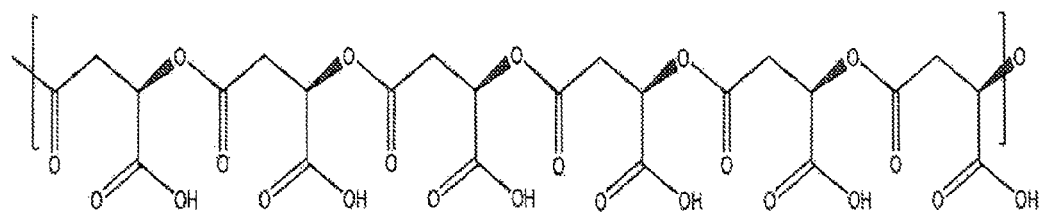
FIG. 2 depicts the structure of poly(β-L-malic acid), or PMLA
Figure 3:
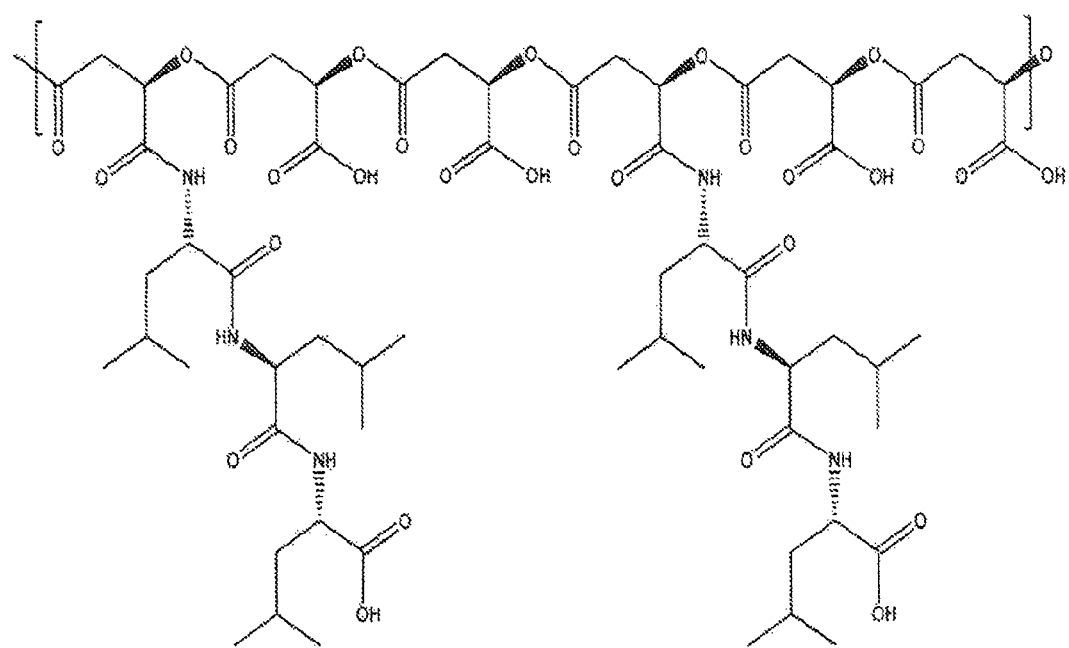
FIG. 3 depicts the structure of PMLA-LLL. Structure of PMLA-LLL.
Figure 4:
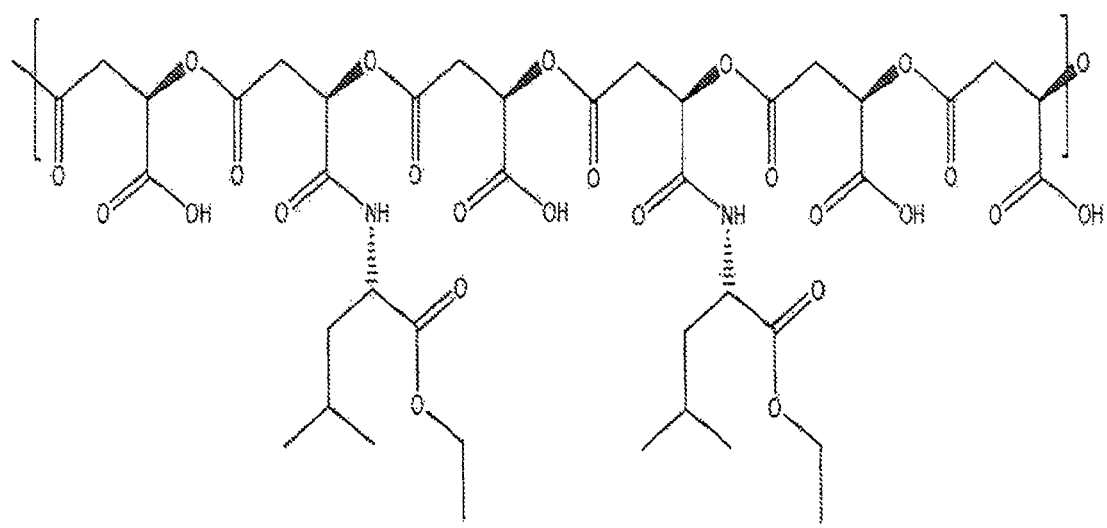
FIG. 4 depicts the structure of PMLA-(LeuOEt). Structure of PMLA-LeuOEt.
Figure 5:
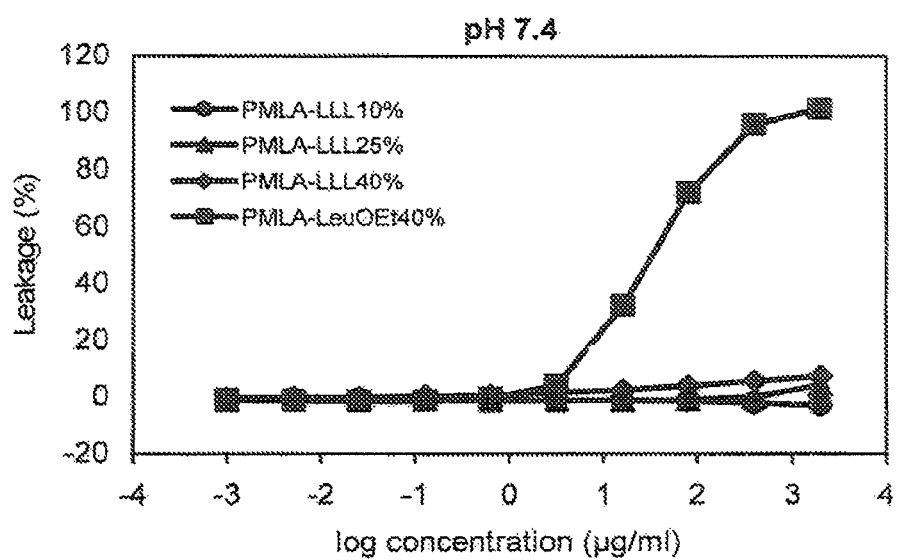
FIGS. 5 (a) and (b) depict charts of results for liposome leakage assay of different polymer conjugates with (a) describing results at a pH of 7.4 and (b) describing results at a pH of 5.0. Concentration dependent liposome leakage by different PMLA conjugates at pH 7.4 and pH 5.0
Figure 5:
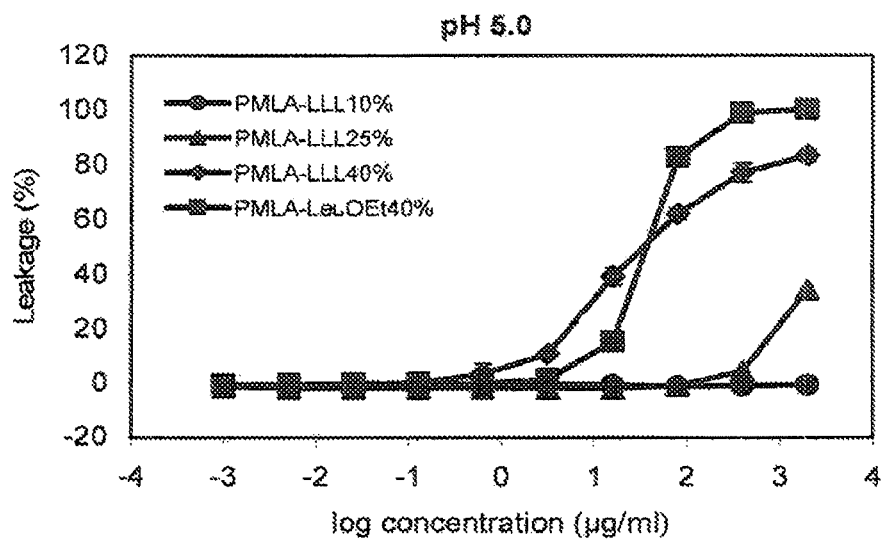
Figure 6:
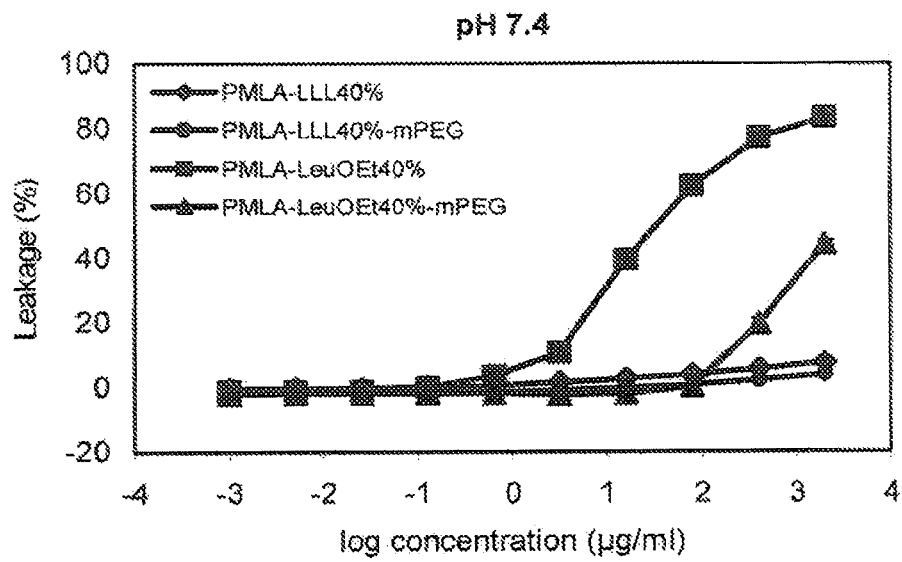
FIGS. 6 (a) and (b) depicts charts demonstrating the effect of mPEG on liposome leakage with (a) describing results at a pH of 7.4 and (b) describing results at a pH of 5.0. Concentration dependent liposome leakage by PMLA conjugates with and without mPEG at pH 7.4 and pH 5.0
Figure 6:
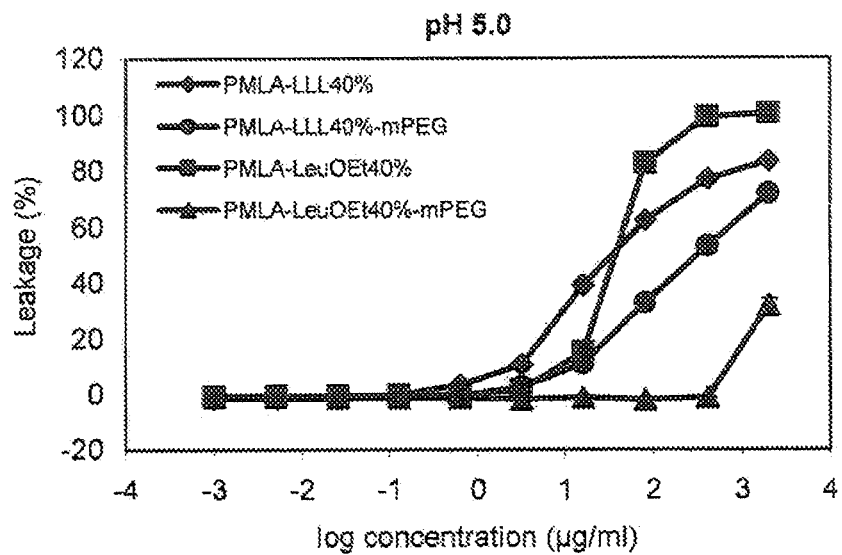
Figure 7:
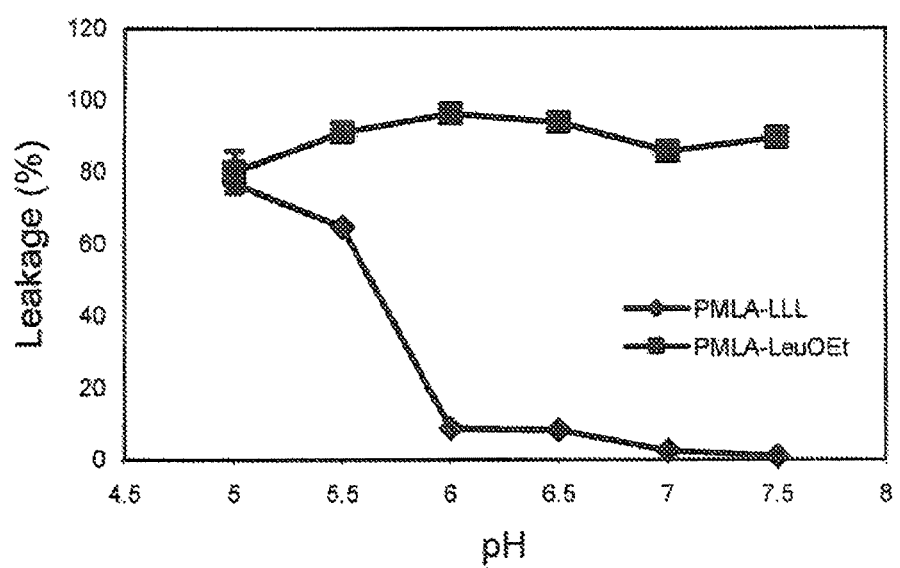
FIG. 7 depicts a chart demonstrating the pH dependence difference between PMLA-LLL and PMLA-LeuOEt. pH dependent liposome leakage of PMLA-LLL40% (50 μg/ml) (.diamond-solid.♦) and PMLA-LeuOEt40% (50 μg/ml) (■).
Figure 8:
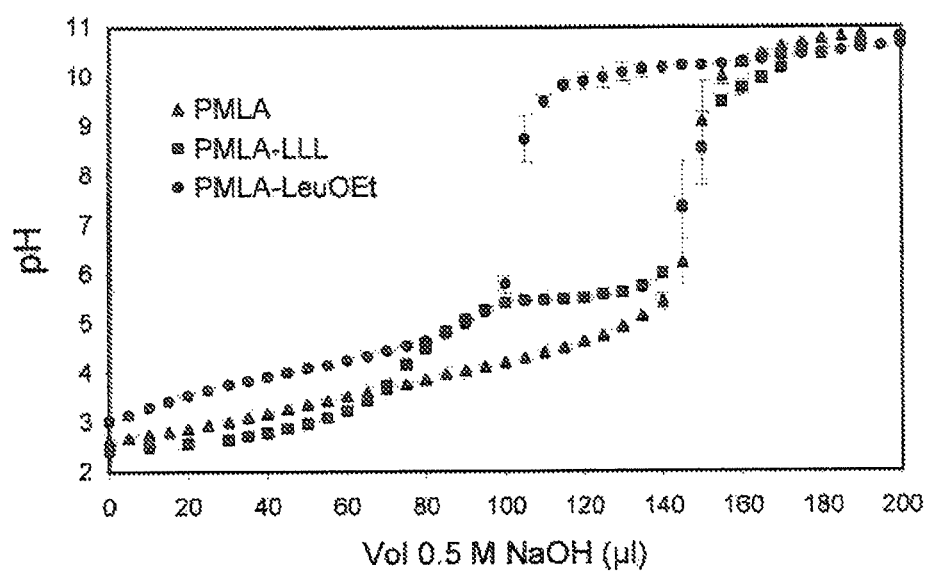
FIG. 8 depicts a chart of pKa titration. Estimation of pKa values of PMLA (▲), PMLA-LeuOEt (♦), and PMLA-LLL (■) by the method of acid-base titration. Only PMLA-LLL shows pKa of 5.5.
Figure 9:
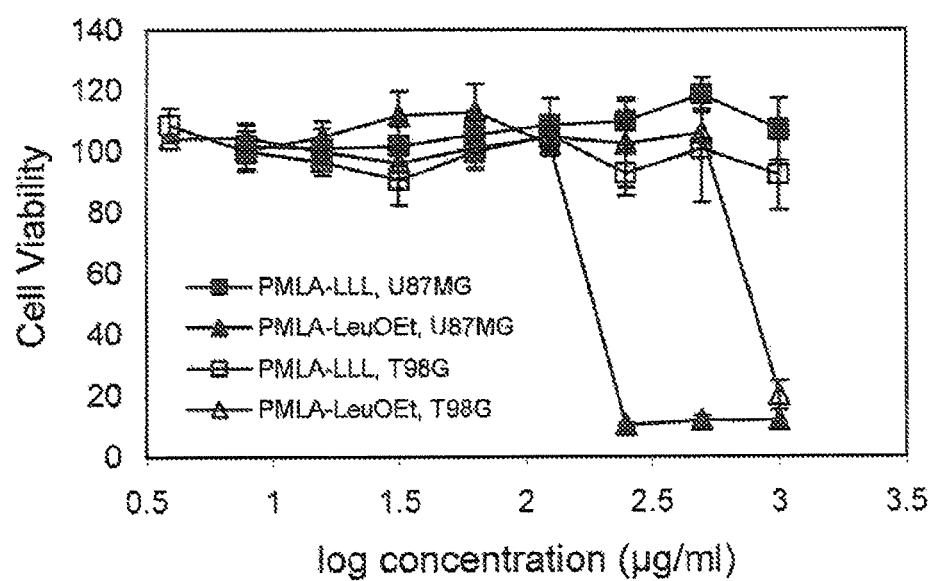
FIG. 9 depicts a chart of cell viability. Cell viability of glioma cell lines U87MG and T98G after treatment with PMLA-LLL or PMLA-LeuOEt
Figure 10:
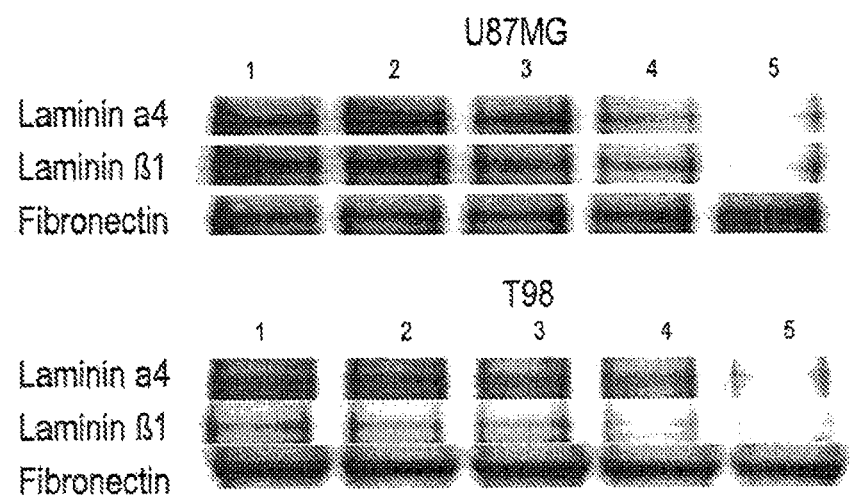
FIG. 10 depicts western blot results, demonstrating cytoplasmic delivery of antisense oligonucleotides. Synthesis of Laminin-411 alpha-4-chains and beta-1-chains by human glioma cell lines U87MG and T98G after treatment with Polycefin variants.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3.sup.rd ed., J. Wiley & Sons (New York, N.Y. 2001); March, Advanced Organic Chemistry Reactions, Mechanisms and Structure 5.sup.th ed., J. Wiley & Sons (New York, N.Y. 2001); and Sambrook and Russel, Molecular Cloning: A Laboratory Manual 3.sup.rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, the term "laminin-411" also means "laminin-8."

As used herein, the term "LLL" is an abbreviation of L-Leu-(L-Leu)-(L-Leu).

As used herein, the term "PMLA" is an abbreviation for poly(13-L-malic acid).

As used herein, the term "PMLA-LLL" includes PMLA containing LLL, which is conjugated by amide bond involving the N-terminal —NH2.

As used herein, the term "PMLA-LLL40%" includes PMLA containing 40% of pendant carboxylates (100%) conjugated by amide bond involving the N-terminal —NH2 of oligopeptide trileucine LLL.

As used herein, the term "Polycefin" is a general name for therapeutic nanoconjugates based on polymalic acid for drug delivery. It may contain multifunctional components, such as a drug a targeting moiety, and an endosome escaping unit.

As used herein, the term "Polycefin-LLL" is a Polycefin variant containing 40% oligopeptide trileucine LLL conjugated as described above.

As used herein, the term "Polycefin-LeuOEt" is a Polycefin variant containing 40% leucine ethyl ester conjugated by amide bond to pendant carboxylates (100%) involving the amino acid ester amino group.

As disclosed herein, naturally occurring PMLA, which is water-soluble, nontoxic, non-immunogenic and biodegradable, was investigated by the inventors for its potential for delivery of cytoplasmic antisense oligonucleotides for cancer treatment. PMLA-LLL40% demonstrated pH-sensitive liposome leakage activity while PMLA containing 10% and 25% trileucine showed no or weak liposome leakage activity. A control polymer, PMLA containing 40% leucine ethyl ester (PMLA-LeuOEt40%) showed liposome leakage activity but in a pH independent manner. In addition, PMLA-LLL40% didn't show toxicity towards human glioma cell lines U87MG and T98G at concentration up to 1 mg/ml in cell viability studies, while PMLA-LeuOEt40% was extremely toxic at high concentration. Therefore, PMLA-LLL40% was tested for cytoplasmic delivery of Morpholino antisense nucleotides against α4 and β1 chains of protein laminin-411, which is overexpressed in gliomas and deposited in newly formed tumor blood vessel basement membranes. Western blot analysis showed that PMLA-LLL containing α4 and β1 Morpholino antisense nucleotides remarkably inhibited secretion of α4 and β1 protein chains of laminin-411 of U87MG and T98G cells, showing that this pH-sensitive Polycefin was able to successfully deliver and liberate the antisense oligos into the cytoplasm.

As further disclosed herein, the Polycefin-LLL is designed to pass through blood brain barrier (BBB) and contains three key components: antisense Morpholino oligonucleotides against laminin-411 α4 and β1 chains, tandem targeting antitransferrin receptor (TfR) antibodies, and new pH-sensitive endosome escape unit, L-leucylleucylleucine (trileucine, LLL). Polycefin variants were injected intravenously in each group of U-87MG cell inoculated mice (n=8 per group). After treatment, the average tumor size of Polycefin-LLL and Polycefin-LeuOEt group was 4 mm$^3$, and 18 mm$^3$, respectively, compared with 47 mm$^3$ in the group treated with PBS ($p<0.01$). The Polycefin-LLL nanoconjugate, which is pH-sensitive, non-toxic, and biodegradable, proves to be the most effective for cytoplasmic delivery of active anticancer agents as compared to previously described Polycefin variants (Lee, B.; Bioconjug Chem 2006, 17, (2), 317-26).

In one embodiment, the present invention provides a method of treating a disease in an individual by injecting intravenously Polycefin-LLL. In one embodiment, the present invention provides a method of inhibiting expression of a protein by administering a therapeutically effective amount of Polycefin-LLL. In another embodiment, the present invention provides a drug delivery molecule, comprising a polymerized carboxylic acid molecular scaffold covalently linked to L-leucylleucylleucine. In another embodiment, the Polycefin-LLL includes antisense morpholino oligos, targeting antibodies, and a pH-sensitive endosome escape unit, In another embodiment, the Polycefin-LLL contains 40% oligopeptide trileucine. In another embodiment, the disease is cancer. In another embodiment, the antisense morpholino oligos include the antisense of laminin-411 α4 and/or β1 chains. In another embodiment, the targeting antibodies include tandem targeting anti-transferrin receptor (TfR) antibodies. In another embodiment, the pH sensitive endosome escape unit includes L-leucylleucylleucine (trileucine, LLL). In another embodiment, the disease is treated by inhibiting expression of laminin-411. In another embodiment, the disease is treated by inhibition of angiogenesis. In another embodiment, the individual is a human. In another embodiment, the individual is a mouse. In another embodiment, the Polycefin-LLL consists essentially of a polymerized carboxylic acid molecular scaffold covalently linked to L-leucylleucylleucine, a pH-sensitive endosome escape unit, a targeting antibody, and an antisense morpholino polynucleotide.

The present invention is also directed to a kit to prepare a drug delivery molecule, as well as the delivery of a drug to the cytoplasm, and may include a polymerized carboxylic acid molecular scaffold, an antisense morpholino oligo, an siRNA, a micro-RNA, an aptamer, a targeting antibody, and L-leucylleucylleucine, and combinations thereof. The kit is an assemblage of materials or components, including least one of the inventive compositions. Thus, in some embodiments the kit contains a composition including PMLA-LLL, as described above.

The exact nature of the components configured in the inventive kit depends on its intended purpose. For example, some embodiments are configured for the purpose of cytoplasmic delivery of active anticancer agents. In one embodiment, the kit is configured particularly for the purpose of cytoplasmic drug delivery to mammalian subjects, such as, but not limited to, human subjects, farm animals, domestic animals, and laboratory animals.

Instructions for use may be included in the kit. "Instructions for use" typically include a tangible expression describing the technique to be employed in using the components of the kit to effect a desired outcome, such as to prepare a PMLA-LLL nanoconjugate and to deliver a drug to a cell cytoplasm. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in preparing a nanoconjugate. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing a solution of PMLA-LLL or components thereof. The packaging material generally has an external label which indicates the contents and/or purpose of the kit and/or its components.

In various embodiments, the present invention provides pharmaceutical compositions including a pharmaceutically acceptable excipient along with a therapeutically effective amount of Polycefin-LLL. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to an intravenous injection, aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Typical dosages of an effective cytoplasmic drug delivery can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

As described herein, various embodiments of the invention include the delivery of a drug to the cytoplasm. As readily apparent to one of skill in the art, the invention may be applied to any number of targets where it would be beneficial to deliver a drug or molecule to the cytoplasm and the invention is in no way limited to nucleotides coding for laminin-411 α4 and/or β1 chains. Similarly, any number of conditions and/or diseases may be beneficially treated and the invention is in no way limited to treatment of cancer, tumor suppression and/or inhibition of glioblastoma angiogenesis. For example, various embodiments described herein may include the treatment of HIV and/or AIDS, and any other number of conditions where it is advantageous to deliver a drug to the cytoplasm. Finally, as would be readily apparent to one of skill in the art, various molecules and/or drugs may also be delivered to the cytoplasm, including the delivery of proteins, and the various embodiments described herein are in no way limited to delivery of antisense morpholino oligo and/or other oligonucleotides. As known to one of skill in the art, protein therapy is often difficult as the protein is unstable or degraded in the liposome before it can be effective, whereas various embodiments described herein overcome these difficulties by allowing deliver of the protein to the cytoplasm.

Various embodiments of the invention may also be practiced in conjunction with an overall treatment regimen. For example, as described herein, various embodiments include the delivery of a drug to the cytoplasm by way of disruption of the endosome. As readily apparent to one of skill in the art, additional drugs or substances that were previously inactive in the endosome will then become active upon the disruption of the endosome. Thus, various embodiments of the invention may include additional drugs or substances administered to the subject being treated and the invention is not only limited to drugs and/or molecules covalently linked to the scaffold as described herein. Similarly, as readily apparent to one of skill in the art, various embodiments of the invention may be used in conjunction with or in combination with additional therapeutics.

As also described herein, various embodiments include intravenous injection of Polycefin-LLL. Intravenous injection provides numerous advantages over most current procedures required for drug delivery past the blood brain barrier. For example, intravenous injection is a less invasive procedure than intracranial injection. However, the invention is in no way limited to intravenous injection and may be administered by any number of methods. For example, the composition may be administered directly in an intra-tumor injection, or by an implantable device, subcutaneously, intraperitoneal, intravenously, or any other methods of administration readily apparent to one of skill in the art.

As readily apparent to one of skill in the art, various embodiments described herein may also be used in conjunction with delivery of siRNA, micro-RNA, and aptamers. PMLA-LLL may act as a transfection agent for cytoplasmic delivery of siRNA, micro-RNA, and aptamers.

Numerous varieties of PMLA-LLL may also be effectively used. For example, liposome leakage activity may be effected by pH levels, or modified due to a higher content of LLL, or other tripeptides, or combination of two or more tripeptides, as well as the length of peptide side chain. Thus, as readily apparent to one of skill in the art, the cytoplasmic drug delivery molecule described in various embodiments herein may be modified depending upon the desired purpose of use and associated conditions, and the invention is not limited to only PMLA-LLL40%.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

General

Naturally occurring poly(β-L-malic acid) (PMLA) is water-soluble, nontoxic, non-immunogenic and biodegradable. As described herein, the inventors investigated its potential for use of cytoplasmic delivery of antisense oligonucleotides for cancer treatment. PMLA containing 40% oligopeptide trileucine (PMLA-LLL40%) demonstrated pH-sensitive liposome leakage activity while PMLA containing 10% and 25% trileucine showed none or weak liposome leakage activity. A control polymer, PMLA containing 40% leucine ethyl ester (PMLA-LeuOEt40%) also showed Liposome leakage activity but in a pH independent manner. In addition, PMLA-LLL40% didn't show toxicity towards human glioma U87MG and T98G cells at concentration up to 1 mg/ml in cell viability studies, while PMLA-LeuOEt40% was extremely toxic at high concentration. Therefore, PMLA-LLL40% was tested for cytoplasmic delivery of Morpholino antisense nucleotides against .alpha.4 and .beta.1 chains of protein laminin-411, which is overexpressed in gliomas and deposited in newly formed tumor blood vessel basement membranes. By western blot analysis Polycefin-LLL containing .alpha.4 and .beta.1 Morpholino antisense nucleotides markedly inhibited the expression of α4 and β1 protein chains of laminin-411 of U87MG cells, showing that this pH-sensitive Polycefin was able to successfully deliver and liberate the antisense oligos into the cytoplasm. This version of Polycefin (Polycefin-LLL) designed to pass through the blood brain barrier (BBB) contains three key components: antisense Morpholino oligos against laminin-411 α4 and β1 chains, tandem targeting anti-transferrin receptor (TfR) antibodies, and the new pH-sensitive endosome escape unit, L-leucylleucylleucine (trileucine, LLL). Polycefin variants were injected intravenously in each group of U87MG cell inoculated mice (n=8 per group). After treatment, the average tumor size of Polycefin-LLL40% group was 4 mm$^3$, compared to 18 mm$^3$ in the group treated with Polycefin-LeuOEt40% (the original version of Polycefin), and 47 mm$^3$ in the group treated with PBS (p<0.01). The newly designed Polycefin-LLL nanoconjugate, which is pH-sensitive, non-toxic, and biodegradable, proved the most effective for cytoplasmic delivery of active anticancer agents.

Example 2

Materials

Morpholino-3' —NH2 antisense oligonucleotides SEQ. ID. NO.: 1 to laminin (MORPH-AON-1) and SEQ. ID. NO.: 2 to laminin β1 (MORPH-AON-2) chains were custom-made by Gene Tools (USA). Rat antimouse monoclonal TfR antibody R17217 (mTfR) and mouse antihuman monoclonal TfR antibody RVS-10 (huTfR) were purchased from Southern Biotech (USA). Poly(β-L-malic acid) (PMLA) (Mw, 100,00; polydispersity 1.3) was obtained from culture broth of *Physarum polycephalum* and was purified and size-fractionated by chromatography. mPEG5000-amine and maleimide-PEG3400-maleimide were obtained from Laysan Bio, Inc. (USA). H-Leu-Leu-OH and H-Leu-Leu-Leu-OH were purchased from Bachem Americas, Inc. (USA). Glioma cell lines U87MG and T98G were obtained from the American Type Culture Collection (USA).

Example 3

Synthesis of PMLA Trileucine Conjugates PMLA-LLL40% and PMLA-LLL40%-MEA

To a 1 ml solution of PIMA 73 mg (0.63 mmol equivalent to malic acid) in acetone was added a mixture of N-hydroxysuccinimide (NHS) and dicyclohexylcarbodiimide (DCC) in 2 ml DMF. After 4 hr stirring at room temperature, dicyclohexylurea was removed by filtration and the volume of reaction solution was reduced to about 0.5 ml with evaporation. Subsequently, to the reaction mixture was added 2 ml pyridine and a solution of H-Leu-Leu-Leu-OH (90 mg, 0.25 mmol, 40% equivalent to the total malyl groups), dissolved with the assistance of 24 µl trifluoacetic acid) in DMF. After 2 hr stirring at room temperature, triethylamine 20 µl was added to the reaction mixture. The completion of conjugation was verified with TLC with ninhydrin test. The unreacted N-hydroxysuccinimidyl ester was hydrolysed by the addition of water. The final product PMLA-LLL40% was purified with PD-10 column (GE Healthcare).

To prepare PMLA-LLL40%-MEA, after the reaction of LLL with PMLA was complete, the unreacted N-hydroxysuccinimidyl ester was not hydrolysed. Instead, 2-mercaptoethylamine hydrochloride (7.2 mg, 0.06 mmol, 10% equivalent to the total malyl groups) (MEA) and triethylamine 9 µl was added to the reaction mixture. The reaction finished within 30 min and the completion of conjugation was verified with TLC with ninhydrin test. Then, the unreacted N-hydroxysuccinimidyl ester was hydrolysed by the addition of water. The final product PMLA-LLL40%-MEA was purified with PD-10 column (GE Healthcare).

Example 4

Synthesis of Polycefin-LLL and Polycefin-LeuOEt

The conjugation of Morpholino oligonuclecotides, antibodies and fluorescence dye to PMLA-LLL40%-MEA and PMLA-LeuOEt40%-MEA to obtain Polycefin-LeuOEt and Polycefin-LLL was described previously (Lee, B.; Bioconjug Chem 2006, 17, (2), 317-26).

Example 5

Lipsome Leakage Assay

Liposome was prepared with extrusion method. Briefly, the mixture of egg PC and cholesterol (molar ratio, 2:1) dissolved in CHCl$_3$/MeOH (v/v, 2:1) was dried under a stream of nitrogen. The lipid mixture was hydrated with HBS buffer (5 mM HEPES, 150 mM NaCl, pH 7.4) containing 90 mM calcein, followed by 19 extrusions through 0.1 µm polycarbonate membrane using mini-extruder (Avanti Polar Lipids). Samples with serial dilutions were dissolved in two 95 µl buffers of different pH in a plate, 137 mM HEPES buffer pH 7.4 and 137 mM citrate buffer pH 5.0, Liposome 5 µl (lipid concentration 160 µM) was added to each sample and the plate was incubated at room temperature for 1 hr. Complete leakage of calcein was achieved with the addition of 0.25% (v/v) triton-X 100 solution of respective buffers. The calcein release was measured with fluorometer with excitation wavelength 488 nm and emission wavelength 535 nm.

Example 6

Cytotoxicity Studies

U87MG and T98G cells were seeded in a 96-well plate (10,000 cells/well in 100 μL media) and incubated for 24 h. Then the cells were incubated with polymers of different concentrations in 200 μL of media for another 24 h. The viable cells were quantified using the CellTiter 96 Aqueous One Solution Cell Proliferation Assay kit (Promega) by reading the absorbance at 490 nm with a Spectra Max Plus 384 ELBA reader.

Example 7

Acid-Base Titration

The pKa values of PMLA, PMLA-LLL40%, and PMLA-LeuOEt40% were estimated with acid-base titration. Polymer conjugates 16 mg were dissolved in 8 ml of deionized water and the pH of solutions were adjusted to low value (around 2). The polymer solutions were titrated with 0.5 N NaOH in 5 μl aliquots. The pH value of polymer solutions after each addition of NaOH was measured after careful mixing and sufficient equilibration.

Example 8

Confocal Microscopy

U87MG cells were plated in a 8 well Lab-Tek II chamber slide containing 200 μl Eagle's MEM with 10% fetal calf serum, Glutamine, sodium bicarbonate, nonessential amino acids, antibiotics, and sodium pyruvate. The cells were incubated with Polycefin-LLL-(SS-Rh) or Polycefin-LLL-Rh with RH (=rhodamine, SS-RH=disulfide conjugated RH) concentration 2 .mu.M for 24 h, 6 h, 2 h, and 0 h. The cells were washed with Dulbecco's modified phosphate-buffered saline (DPBS) for 5 times and fixed with 2% paraformaldehyde for 10 min followed by washing with DNS three times. The cells were visualized with TCS SP spectral scanner (Leica Microsystems, Mannheim, Germany).

Example 9

Western Blotting

Human glioma U87MG and T98 produce secreted laminin 411. Polycefin-LLL or the other variants at a concentration of 1.4 μM MORPH-AON was added to the culture medium of these cultured cell lines on day 1 and 4. For the detection of laminins, serum-free conditioned medium was sampled at day 6 from culture supernatants above equal numbers of cells that has been cultured for the same period of time. Samples were concentrated 10-fold by filtering through Centriplus filtration devices (Millipore, Bedford, Mass.) and proteins were separated using Tris-Glycine 8% SDS-PAGE (Invitrogen) under reducing conditions. The gels were blotted onto nitrocellulose membrane (Invitrogen). The membranes were probed with mAbs followed by chemiluminescent detection using the Immune-Star kit with alkaline phosphatase-conjugated secondary antibodies (Bio-Rad Hercules, Calif.). Antibodies were used to laminin α4 [mAb 8B12] and β1 chains (mAb LT3). Antibody to human fibronectin $8^{th}$ type III repeat [mAb 568] was used to control for equal loading of gel lanes.

Example 10

Imaging

The imaging procedures for drug accumulation in mice tumors were same as previously reported.[30] Briefly, 5×10$^4$ of U87MG human glioblastoma cells were stereotactically implanted into the right basal ganglia field of athymic mice (CrTac:NCr-Foxnlnu Homozygous, Taconic, USA). At day 2I after tumor implantation, 100 μl of AlexaFluor 680 labeled Polycefin variants was injected intravenously at the concentration of 3 μM. For assessment of drug distribution and localization in nude mice, Xenogen IVIS 200 was used under the Isoflurane anesthesia at different time points (before drug administration; 1 h, 3 h, 6 h, 24 h, 48 h after drug administration). Twenty-four hours after drug administration, the mice were euthanized and the circulating drugs in blood vessels were eliminated by intraarterial PBS perfusion for 20 min. The brain was harvested to detect the fluorescent signal. The fluorescent signal intensities in the tumor, tumor adjacent area, normal cerebrum and normal cerebellum were analyzed by Xenogen Living Image, Version 2.50 (WaveMetrix, USA). All animal procedures were carried out in accordance with IACUC protocols approved by animal welfare committee at Cedars-Sinai Medical Center.

Example 11

Tumor Suppression

U87MG human glioblastoma cells (5×1.0$^4$) were stereotactically implanted into the right basal ganglia field of athymic mice (n=8 per group) (CrTac:NCr-Foxnlnu Homozygous, Taconic, USA). After day 8, Polycefin variants were injected intravenously at dose of 5 mg/kg AONs to laminin-411 α4 and β1 chains every three days for 8 injections in total. Mice in all Polycefin- and PBS-treated groups were sacrificed on day 48 after tumor cell inoculation and tumor size was measured.

Example 12

Results—Synthesis of PMLA-LLL

The synthesis of PMLA-LLL is simple conjugation of polymalic with trileucine peptide. The carboxyl group of PMLA was activated with DCC and NHS to form N-hydroxysuccinimidyl esters which is substituted by the amino group of trileucine. Trileucine, however, is not readily dissolved in reaction compatible solvent such as DMF and DMSO. To solve this, it was first dissolved in DMF with the assistance of 1.25 equivalent of trifluoroacetic acid and excess of pyridine was used as base. The completeness of the reaction was monitored with ninhydrin test. The addition of triethyl amine was to facilitate the completion of the reaction.

Example 13

Results—Liposome Leakage Assay

Liposome leakage assay was used for the membrane destabilizing activity of various PMLA conjugates. PMLA conjugates containing 10%, 25% and 40% of trileucine were prepared and their membrane destabilizing activity was evaluated using liposome leakage assay. PMLA-LLL10% didn't show liposome leakage at the tested concentrations at both pH 7.4 and pH 5.0. PMLA-LLL25% and PMLA-LLL40% showed little liposome leakage activity even at concentration as high as 2 mg/ml (less than 10% leakage) at pH 7.4. In contrast, PMLA-LLL40% showed significant liposome leakage at pH 5.0 from low concentration (1 μg/ml) to high concentration (2 mg/ml) and about 50% liposome leakage was observed at concentration of 20 μg/ml. PMLA-LLL25%, however, only showed Liposome leakage activity at high concentration. Therefore, the content of LLL is important in modulating the liposome activity of PMLA-LLL conjugates: the higher the content of LLL, the more efficient for liposome leakage. To see the length effect of peptide chain on liposome leakage activity, PMLA conjugates containing dileucine LL40% and tetraleucine LLLL40% were also tested. However, neither conjugates (PMLA-LL40%) and (PMLA-LLLL40%) showed significant liposome leakage at both pH 7.4 and pH 5.0, showing that the length of peptide chain is also important for the liposome leakage activity, with the chain length of the tripeptide optimal for liposome leakage.

Meanwhile, liposome leakage was also evaluated for a control polymer PMLA-LeuOEt40%, a PMLA conjugate containing 40% leucine ethyl ester previously proposed for endosome disruption. At pH 5.0, PMLA-LeuOEt40% showed a similar liposome leakage profile to that of PMLA-LLL40%, but with less liposome activity at low concentration and with higher activity at high concentration compared with PMLA-LLL40%. Unlike PMLA-PMLA-LeuOEt40% also showed good liposome leakage activity at pH 7.4. Consequently, the liposome leakage activity of PMLA-LLL40% is pH sensitive, while that of PMLA-LeuOEt40% is pH insensitive.

Therefore, the pH sensitivity of liposome leakage was also evaluated for both PMLA-LLL40% and PMLA-LeuOEt40%. Liposome leakage activity of each polymer was tested at concentration of 50 μg/ml and at pH values ranging from 5.0 to 7.5, representing the pH values which polymers will encounter during endocytosis. PMLA-LLL40% virtually showed no liposome leakage activity at pH 7 and 7.5 and started to show slight activity at pH 6 and 6.5. When pH is lower than 5.5, strong liposome leakage was observed (>60%). PMLA-LeuOEt40% demonstrated strong liposome leakage activity (>80%) at all pHs tested, showing it can destabilize membrane not only at endosomal pH but also at physiological pH. Therefore, the liposome leakage activity of PMLA-LLL is pH sensitive; while that of PMLA-LeuOEt is pH insensitive. The pH insensitivity of PMLA-LeuOEt may cause the cytotoxocity due to its capability to destabilize cell membrane at physiological pH.

Example 14

Results—Effect of mPEG on Liposome Leakage

Polyethyleneglycol (PEG) is widely used for protection of degradation of nanoconjugates, and previously it was also used for the protection of PMLA conjugate. However, how the PEGylation or PMLA may affect the membrane destabilization activity of the whole conjugate is unknown. It is necessary to resolve this to optimize the cytoplasmic delivery capability of newly designed conjugate. PEGylation had virtually no effect on the liposome leakage of PMLA-LLL40% at pH 7.4; however, at pH 5.0, more than 10-fold of PMLA-LLL-mPEG has to be used to achieve same amount of liposome leakage induced by PMLA-LLL. In contrast, the liposome activity of PMLA-LeuOEt was affected by PEGylation at both pH 7.4 and pH 5.0. In addition, the PEGylation of PMLA-LeuOEt had a more negative effect on liposome leakage. At both pHs, more than 100-fold of PMLA-LeuOEt-mPEG has to be used to achieve same amount of Liposome leakage induced by PMLA-LeuOEt.

Example 15

Results—Cytotoxicity

To evaluate the cytotoxicity of PMLA-LLL40% and PMLA-LeuOEt40%, two human glioma cell lines, U87MG and T98G, were treated with each conjugate of different concentrations. Viable cells were determined using CellTiter 96 Aqueous One Solution Cell Proliferation Assay kit (Promega). PMLA-LLL/40% didn't show any cytotoxicity towards both cell lines at all concentrations tested up to 1 mg/ml. Although PMAL-LeuOEt40% didn't show significant cytotoxicity at concentrations lower than 100 μg/ml, its cytotoxicity increased drastically at concentrations higher than 125 μg/ml for U87MG cells and higher than 500 μg/ml for T980 cells. After the treatment of cells with polymers (500 μg/ml) for 24 h, U87MG cells treated with PMLA-LLL40% looked healthy without any morphological changes. Instead, cells treated with PMLA-LeuOEt40% at toxic concentration were all dead and showed cell shapes typical of necrosis. Based on cytotoxicity results, PMLA-LLL40% is safer than PMLA-LeuOEt40% when used in drug delivery.

Example 16

Results—Detection of Laminin Expression by Western Blot Analysts

Western blot was used to confirm that the newly designed nanoconjugate can achieve cytoplasmic delivery of antisense oligonucleotides. Cultures of two human glioma cell lines, U87MG and T98G were treated with Polycefin variants. Polycefin-LeuOEt and Polycefin-LLL are PMLA conjugates containing the nonspecific membrane escape unit LeuOEt or the endosome specific escape unit LLL and, in addition, Morpholino antisense oligos, anti-transferrin receptor antibodies. Inhibition of laminin-411 synthesis by Polycefins was determined by western blotting. Fibronectin was used as an internal reference to correct for equal loading of samples. In the absence of endosome escape unit, PMLA conjugated with Morpholino oligo only (lane 2) or with PMLA-(TfR mAb)-AON (lane 3), didn not significantly inhibit the synthesis α4 and β1 chains of lamini-411 compared with no treatment (lane 1). Both Polycefin-LeuOEt (lane 4) and Polycefin-LLL (lane 5) inhibited the synthesis of laminin-411. Polycefin-LLL showed the strongest inhibition. The inhibition by Polycefin-LLL is in accordance with cytoplasmic delivery of Morpholino oligos. The results demonstrate the safe and efficient delivery of nucleic acid based drugs by Polycefin-LLL.

Example 17

Results—Selective Accumulation of Polycefin in Tumor

Figure 11:
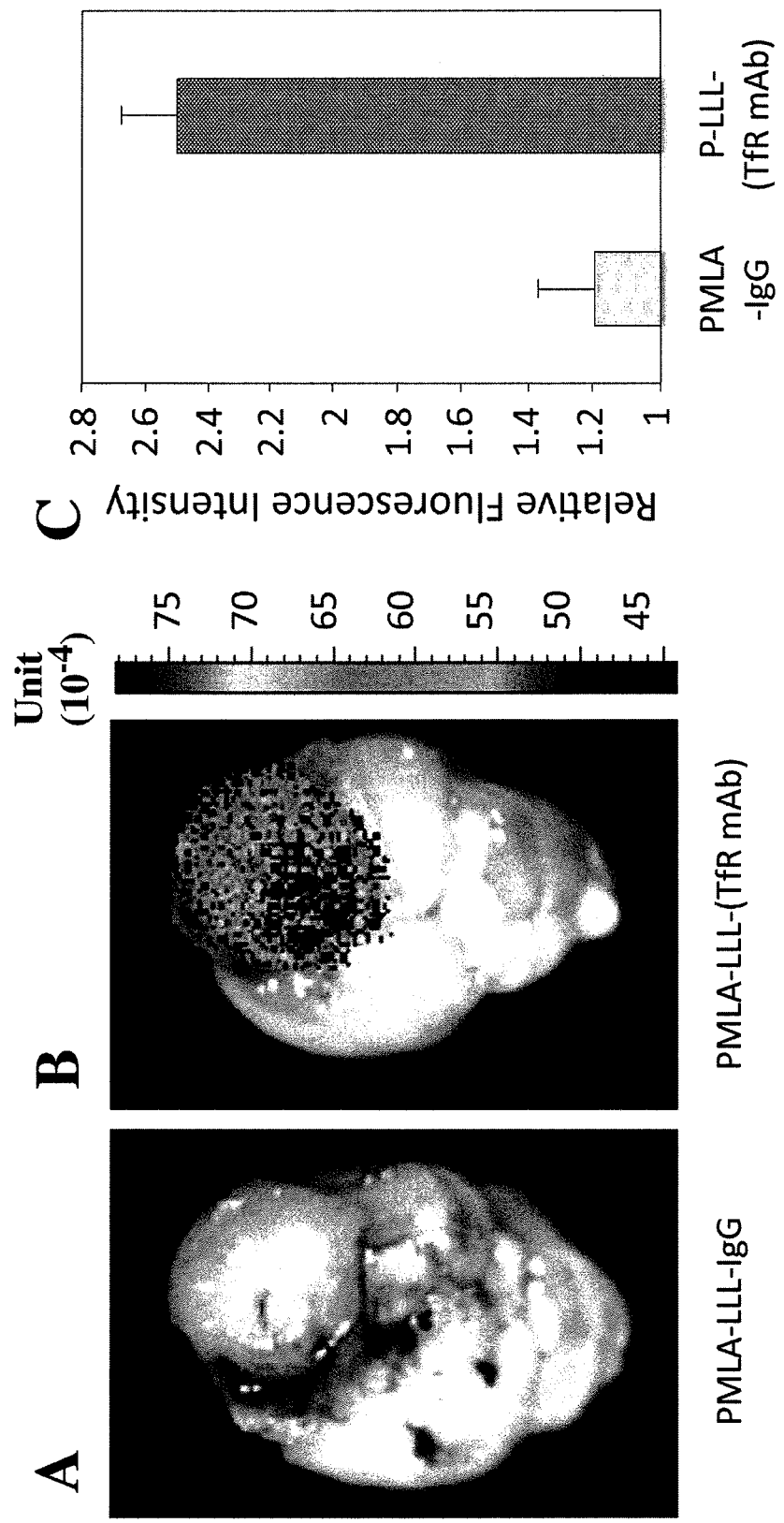
FIG. 11 depicts the imaging of enhanced accumulation of PMLA-LLL containing tansferrin receptor antibody at brain tumor Selective accumulation in brain tumor of PMLA-LLL containing unspecific IgG (control) in panel A or anti-transferrin antibody (TfR mAb) in panel B. Fluorescence intensities are shown for the conjugated tracer in panel C.
Figure 12:
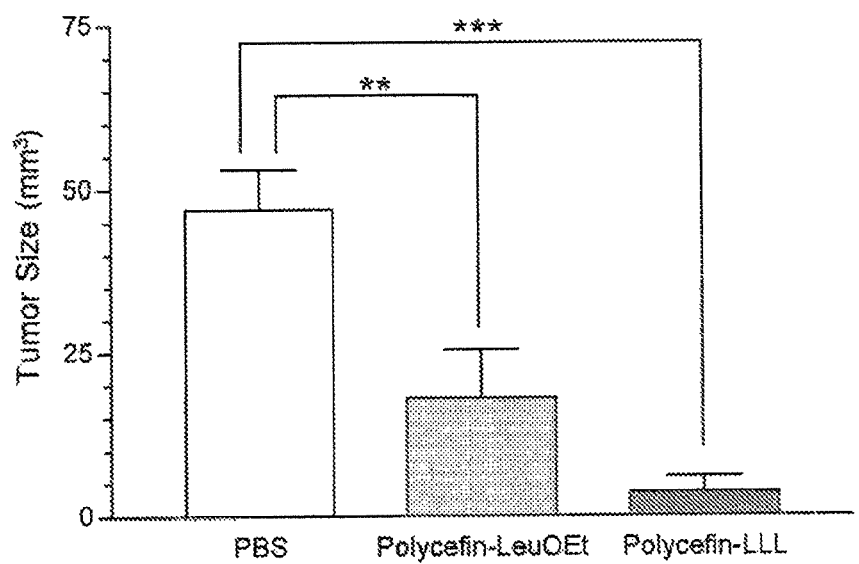
FIG. 12 depicts a chart describing tumor volume after various intravenous treatments ($mm^3$, mean±SEM). Growth suppression of implanted human brain tumor after treatment with PBS (control) or different Polycefin variants (Anova test, p<0.01).

To confirm that Polycefin-LLL crossed selectively blood-brain-tumor barrier with the result to be selectively accumulated only in brain tumor, the inventors carried out intravenous injections into human brain tumor-bearing nude mice and monitored its distribution. In these experiments, the inventors used Alexa Fluor 680 conjugated PMLA-LLL40% containing transferrin receptor antibody. In control experiments, transferrin receptor antibody was replaced by unspecific mouse IgG. Xenogen IVIS 200 imaging system was used to detect the drug distribution in whole body and isolated mouse organs 24 h after injection. Repeated experiments were conducted, giving qualitatively the same results. As shown in FIG. 11, PMLA-LLL40% containing transferrin receptor antibody was selectively accumulated at the tumor site, and its accumulation was significantly higher than that of the control conjugate containing the nonspecific IgG after 24 ($P<0.01$).

Example 18

Results—Tumor Suppression Study

Laminin-411 is associated with glioma recurrence and shorter patient survival time, and it is important for glioblastoma angiogenesis. In vivo inhibition of laminin-411, therefore, provides a safe and effective way to suppress tumor growth. Mice were treated with two Polycefin variants, Polycefin-LeuOEt and Polycefin-LLL and were sacrificed on day 48 after tumor cell inoculation. After sacrifice of mice, their tumor size was measured. Treatment with Polycefin-LeuOEt significantly suppressed the brain tumor growth with average tumor size of 18 $mm^3$ compared with 47 $mm^3$ in the control group treated with PBS (one way Anova test, $p<0.01$). Moreover, the treatment with Polycefin-LLL suppressed the tumor growth to an even larger extent at high significance (average tumor size 4 $mm^3$, $p<0.001$). The results show that Polycefin-LLL delivers anticancer agents not only in vitro but also in vivo. Because this carrier favors delivery through endosomes it is considered a safe and efficient cytoplasmic device for delivery of nucleic acid based drugs and proteins.

Various embodiments of the invention are described above in the Description of the Invention. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

```
Sequence CWU 1
2125DNAHomo sapiens
1agctcaaagc catttctccg ctgac

25225DNAHomo sapiens
2ctagcaactg gagaagcccc atgcc 25
```

What is claimed is:

1. A method of decreasing the volume of a tumor in an individual, comprising:
providing a composition including a drug delivery system configured to destabilize an endosome membrane, wherein the drug delivery system comprises a polymerized polymalic acid molecular scaffold having a plurality of pendant carboxyl groups and one or more biologically active molecular modules, wherein the one or more biologically active molecular modules includes L-leucylleucylleucine and an anticancer agent, each of the one or more biologically active molecular modules is covalently linked to a pendant carboxyl group of the polymerized polymalic acid molecular scaffold; and
administering the composition to the individual.

2. The method of claim 1, wherein the anticancer agent comprises a nucleic acid-based therapeutic.

3. The method of claim 1, wherein the tumor is a glioma.

4. The method of claim 2, wherein the nucleic acid-based therapeutic inhibits protein synthesis of laminin-411.

5. The method of claim 4, wherein the nucleic acid-based therapeutic comprises a Laminin α4 antisense polynucleotide and/or β1 antisense polynucleotide.

6. The method of claim 5, wherein the Laminin α4 antisense polynucleotide comprises the 5' to 3' polynucleotide sequence described as SEQ. ID. NO.: 1.

7. The method of claim 5, wherein the Laminin β1 antisense polynucleotide comprises the 5' to 3' polynucleotide sequence described as SEQ. ID. NO.: 2.

8. The method of claim 5, wherein the one or more biologically active molecular modules further comprises a targeting antibody.

9. The method of claim 1, wherein the step of providing the composition includes synthesizing the drug delivery system, comprising providing a quantity of a L-leucylleucylleucine; providing a quantity of a polymalic acid; and conjugating the L-leucylleucylleucine with the polymalic acid.

10. The method of claim 9, wherein the polymalic acid comprises PMLA.

11. The method of claim 9, wherein L-leucylleucylleucine is conjugated with the polymalic acid by an amide bond.

12. The method of claim 8, wherein the step of administering comprises delivering the composition to the individual at a concentration of up to 1 mg/mL.

13. The method of claim 1, wherein the composition is administered systemically.

14. The method of claim 1, wherein the composition is administered near the tumor.

15. The method of claim 1, wherein the composition is administered by an intra-tumoral injection.

16. The method of claim 1, wherein the composition is administered by an implantable device from which the composition elutes.

17. The method of claim 1, wherein the composition is administered subcutaneously, intraperitoneally and/or intravenously.

* * * * *